US 7,026,337 B2
Bohn et al.
Apr. 11, 2006

(54) ANTIMYCOTIC GEL HAVING HIGH ACTIVE COMPOUND RELEASE

(75) Inventors: Manfred Bohn, Hofheim (DE); Karl Theodor Kraemer, Langen (DE); Astrid Markus, Liederbach (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 198 days.

This patent is subject to a terminal disclaimer.

(21) Appl. No.: 10/690,597

(22) Filed: Oct. 23, 2003

(65) Prior Publication Data

US 2004/0081677 A1    Apr. 29, 2004

Related U.S. Application Data

(62) Division of application No. 09/068,894, filed as application No. PCT/EP97/05068 on Sep. 16, 1997.

(30) Foreign Application Priority Data

Sep. 27, 1996    (DE) ................................. 196 39 816

(51) Int. Cl.
    *A61K 31/4412*    (2006.01)
    *A61P 31/10*    (2006.01)

(52) U.S. Cl. ....................... 514/345; 514/944
(58) Field of Classification Search ................ 514/345, 514/944; 424/484–88
See application file for complete search history.

(56) References Cited

U.S. PATENT DOCUMENTS

| 3,968,118 A | 7/1976 | Lohaus et al. |
| 4,185,106 A | 1/1980 | Dittmar et al. |
| 4,699,924 A | 10/1987 | Durrant et al. |
| 4,797,409 A | 1/1989 | Lohaus et al. |
| 4,957,730 A | 9/1990 | Bohn et al. |
| 5,066,484 A | 11/1991 | Castrogiovanni et al. |
| 5,071,639 A | 12/1991 | Soyama et al. |
| 5,120,530 A | 6/1992 | Ferro et al. |
| 5,132,107 A | 7/1992 | Lange |
| 5,264,206 A | 11/1993 | Bohn et al. |
| 5,346,692 A | 9/1994 | Wohlrab et al. |
| 5,356,907 A | 10/1994 | Clemence et al. |
| 5,395,843 A | 3/1995 | Clemence et al. |
| 5,494,658 A | 2/1996 | Hänel et al. |
| 5,510,100 A | 4/1996 | Picard et al. |
| 5,559,130 A | 9/1996 | Clemence et al. |
| 5,603,939 A | 2/1997 | Ser |
| 5,609,854 A | 3/1997 | Guerrero et al. |
| 5,612,327 A | 3/1997 | Makino et al. |
| 5,650,145 A | 7/1997 | Saint-Leger |
| 5,675,013 A | 10/1997 | Hani et al. |
| 5,683,681 A | 11/1997 | Ramin et al. |
| 5,753,600 A | 5/1998 | Kamegai et al. |
| 5,756,108 A | 5/1998 | Ribier et al. |
| 5,866,105 A | 2/1999 | Richter et al. |
| 6,162,420 A | 12/2000 | Bohn et al. |
| 6,455,551 B1 | 9/2002 | Kraemer et al. |
| 6,469,033 B1 | 10/2002 | Bohn et al. |
| 2003/0086881 A1 | 5/2003 | Bohn et al. |
| 2004/0039030 A1 | 2/2004 | Bohn et al. |

FOREIGN PATENT DOCUMENTS

| AU | 716 208 | 4/1998 |
| CA | 2134293 | 4/1995 |
| CA | 2134304 | 4/1995 |
| DE | 31 40 954 A1 | 5/1983 |
| DE | 38 26 914 A1 | 2/1990 |
| EP | 0 218 410 A3 | 4/1987 |
| EP | 0 241 918 A2 | 10/1987 |
| EP | 0 313 305 | 4/1989 |
| EP | 0 381 446 A1 | 8/1990 |
| EP | 0 515 312 A2 | 11/1992 |
| EP | 0 646 369 A1 | 4/1995 |
| EP | 0 649 660 A3 | 4/1995 |
| EP | 0 680 745 A2 | 11/1995 |
| EP | 0 680 745 A3 | 11/1995 |
| EP | 0 771 187 B1 | 5/1997 |
| FR | 2 618 068 | 1/1989 |
| FR | 2 685 638 | 7/1993 |
| FR | 2 685 867 | 7/1993 |
| FR | 2 694 694 A1 | 2/1994 |

(Continued)

OTHER PUBLICATIONS

Abrams et al., "Ciclopirox Olamine: A Hydroxypyridone Antifungal Agent," *Clinics in Dermatology*, vol. 9, pp. 471-477 (1992).

(Continued)

*Primary Examiner*—Edward J. Webman
(74) *Attorney, Agent, or Firm*—Finnegan, Henderson, Farabow, Garrett & Dunner, L.L.P.

(57) ABSTRACT

A pharmaceutical preparation comprising a hydrophilic gel-forming agent, water and a compound of the formula I (I)

$$\text{(pyridone structure with substituents } R^1, R^2, R^3, R^4 \text{ and N-OH)}$$

is suitable for the treatment and prophylaxis of dermatomycoses.

5 Claims, No Drawings

FOREIGN PATENT DOCUMENTS

| | | |
|---|---|---|
| GB | 2 207 051 | 1/1989 |
| GB | 2 208 149 A | 3/1989 |
| HU | 202 098 B | 3/1990 |
| HU | 208 007 B | 5/1991 |
| JP | 61-69721 | 4/1986 |
| WO | WO 87/02580 A | 5/1987 |
| WO | WO 94/05256 | 3/1994 |
| WO | WO 95/17165 | 6/1995 |
| WO | WO 96/02226 A1 | 2/1996 |
| WO | WO 96/13247 | 5/1996 |
| WO | WO 96/19186 | 6/1996 |
| WO | WO 96/29045 | 9/1996 |
| WO | WO 96/29056 | 9/1996 |
| WO | WO 97/20560 | 6/1997 |
| WO | WO 98/13009 | 4/1998 |
| WO | WO 98/13042 | 4/1998 |
| WO | WO 98/13043 | 4/1998 |
| WO | WO 99/39680 A | 8/1999 |
| WO | WO 99/49835 | 10/1999 |

OTHER PUBLICATIONS

Aly et al., "Common Superficial Fungal Infectious in Patients with AIDS," *Clin. Infect. Diseases*, vol. 22, Suppl. 2, pp. S128-S132 (1996).

Amos et al., "Clinical efficacy of Polytar AF (Fongitar) and Nizoral Scalp Treatments in Patients with Dandruff/Seborrhoeic Dermatitis," *Journal of Dermatological Treatment*, vol. 5, pp. 127-130 (1994).

Braga et al., "Inhibition of Candida Albicans Adhesiveness to Human Buccal and Vaginal Cells by Sub-inhibitory Concentrations of Rilopirox," *Arzneim.-Forsch./Drug Res.*, vol. 45, No. 1, pp. 84-87 (1995).

Corte et al., "Topische Anwendung einer 0.1%igen Ciclopiroxolamin-Lösung zur Behandlung der Pityriasis versicolor, Topical Application of a 0.1% Ciclopiroxolamine Solution for the Treatment of Pityriasis versicolor," *Mycoses*, vol. 32, No. 4, pp. 200-203 (1989). (English Abstract).

Cullen et al., "Treatment of Tinea Versicolor with a New Antifungal Agent, Ciclopirox Olamine Cream 1%," *Clinical Therapeutics*, vol. 7, No. 5, pp. 574-583 (1985).

Faergemann, J., "Pityriasis Versicolor," *Seminars in Dermatology*, vol. 12, No. 4, pp. 276-279 (1993).

Grosshans et al., "L'Eczema Seborrheique (La Pityrosporose)," *Ann. Dermatol. Venereol.*, vol. 115, pp. 79-86 (1988). (English Abstract).

Hanel et al., "Evaluation of Fungicidal Action *in Vitro* and in a Skin Model Considering the Influence of Penetration Kinetics of Various Standard Antimycotics," *Annals New York Academy of Sciences*, vol. 544, pp. 329-337 (1988).

Hanel et al., "A Comparison of Bifonazole and Ciclopiroxolamine: *in Vitro*, Animal, and Clinical Studies," *Mycoses*, vol. 31, No. 12, pp. 632-640 (1988).

Hanel et al., "Treatment of Seborrhoic Eczema Using an Antimycotic with Antiphlogistic Properties," *Mycoses*, vol. 34, Suppl. 91-93 (1991). (English Summary).

Martindale, The Extra Pharmacopoeia 30th Ed., London, *The Pharmaceutical Press*, pp. 332, 1609 (1993).

Montana et al., "A Double-Blind, Vehicle-Controlled Study of the Safety and Efficacy of Fungoid Tincture® in Patients with Distal Subungual Onychomycosis of the Toes," *Cutis*, 53:313-316 (1994).

Plewig et al., "Seborrheic Dermatitis," *FitzPatrick's Dermatology in General Medicine*, 5th Ed., Ch. 126, pp. 1-17 CD-Rom (1999).

Przekop et al., "Ciclopirox Olamine, An Antifungal Modulator of Neutrophil Function and Infiltrate in Cutaneous Inflammation," *J. Investigative Dermatology*, vol. 102, No. 4, (SID Abstracts) p. 593, (1994).

Raether et al., "Riopriox-a New Hydroxypyridone Antifungal with Fungicidal properties," *Mycoses*, vol. 33, No. 4, pp. 191-202 (1990).

Rivalland, P., et al., "Evaluation of the antifungal activity of two derivatives and in vivo innocuity tests of shampooings with regard to antidandruff formulations," Abstract, *Int. J. Cosmet. Sci.*, vol. 16, No. 2, pp. 77-83 (1994).

Saint-Leger et al., "the Role of the Resident Microflora in the Pathogenesis of Dandruff," *J. Soc. Cosmet. Chem.*, vol. 40, No. 2, pp. 109-117 (1989).

Schofer, H., "Therapie des seborrhoischen Ekzems bei HIV-Infektion," Forschung und Praxis, 98 Seite III, (1990).

Shapiro et al., "Medicated Shampoos," *Clinics in Dermatology*, vol. 14, pp. 123-128 (1996).

Shuster, S., "Dandruff, Seborrhoeic Dermatitis, and Pityrosporum Ovale," *Cosmetics and Toiletries*, vol. 103, pp. 87-91 (1988).

Yoshimasa et al., "the Sebum Lipid Assimilation and The Growth Inhibition of *Pityrosporum ovale* (1st report)," *J. Soc. Cosmet. Chem. Japan*, vol. 22, No. 3, pp. 165-170 (1988). (English Abstract).

"Scaly Dermatoses," *Handbook of Nonprescription Drugs*, American Pharm. Assoc., Ch. 26, pp. 550-552 (1996).

"Seborrheic Dermatitis and Dandruff," Manual of Dermatologic Therapeutics, 5th Ed., Ch. 29, pp. 164-167 (1995).

Abstract of JP 07-082126 A (1993).

U.S. Appl. No. 09/077,194, filed May 26, 1998, Bohn et al.

Derwent Abstract No. 95-325488 for JP 07 223 971 A (Aug. 22, 1995).

ANTIMYCOTIC GEL HAVING HIGH ACTIVE COMPOUND RELEASE

This is a division of, and claims benefit of priority under 35 U.S.C. § 120 of, U.S. application Ser. No. 09/068,894, filed Sep. 18, 1998, which is a national stage application under 35 U.S.C. 371 of PCT/EP97/05068, filed Sep. 16, 1997. This application also claims benefit of priority under 35 U.S.C. § 119 of Application No. 196 39 816.9, filed in Germany on Sep. 27, 1996. All of the foregoing applications are incorporated herein by reference.

The present invention relates to a topically applicable antimycotic preparation having high active compound release in the form of a gel preparation which contains at least one antimycotic substance from the hydroxypyridone class and at least one hydrophilic gel-forming agent.

For the topical treatment of mycoses, especially mycoses of the skin, various preparation forms of hydroxypyridone derivatives such as solutions, ointments and powders are already known. Optimum treatment of dermatomycoses, however, using the preparation forms of hydroxy-pyridones known until now is not unrestrictedly possible for the most diverse reasons.

Topically applicable liquid preparations in general include clear aqueous or aqueous-alcoholic solutions. They are either painted onto the skin surface or used for washing or baths. In particular, they are used in any skin regions which are covered by dense hair growth, since ointments or powders are not suitable for these areas. Moreover, they are used in those skin areas for which other pharmaceutical forms are not willingly used for cosmetic reasons, e.g. on the face or on highly mobile body sites (e.g. elbows, knee etc.).

The release rate of the active compound from solutions is generally high, since after application by evaporation of the vehicle constituents a high concentration gradient between the preparation and the skin results, which in the end leads to a high absorption of active compound through the skin and thus to a high efficacy.

With respect to their applicational properties, solutions, however, are rather to be assessed as less favorable, since on account of their liquid aggregate state they can only be handled with difficulty, in particular on the face, and a specific application to restricted skin areas is not possible.

Ointments or semisolid pharmaceutical forms are administration forms which in general are spreadable in the temperature range between room temperature and skin temperature and thereby can be differentiated from the liquid administration forms and those with solid character. Based on the substance characteristics of the skin vehicle substances, ointments are in general understood as meaning anhydrous fatty bases or emulsions consisting of an oily and aqueous phase, which are stabilized by an emulsifier.

On account of their semisolid consistency, ointment preparations—in contrast to solutions—can be applied very specifically to restricted skin areas. Owing to the content of fatty constituents, however, the release of the lipophilic hydroxypyrrolidone derivatives from the ointment constituents is highly restricted. The success of treatment after ointment application is furthermore adversely affected by the fact that ointments do not usually leave behind a wipe-resistant film on the skin. On contact with the clothing or bed linen, the product applied can thus be easily removed again and is thus no longer available for successful therapy.

Powder preparations are primarily used for the adsorption of increased secretion and keeping the skin dry; a point which, in particular in the treatment of dermatomycoses, plays an important part. For practical reasons, the application of powder preparations is almost exclusively restricted to the treatment of mycosis pedis.

It has now been found that gel formulations of hydroxypyridone derivatives, which contain solvents and hydrophilic gel-forming agents and also customary formulation auxiliaries, make possible a high release of the active compound and thus an improved action due to the achievement of high concentrations of the active compound in the skin. The preparations according to the invention can furthermore be applied to the affected skin areas easily and specifically on account of their semisolid consistency and moreover exhibit the desired drying-out effect, particularly in the treatment of mycosis pedis.

The invention therefore relates to a pharmaceutical preparation comprising a hydrophilic gel-forming agent, water and a compound of the formula I

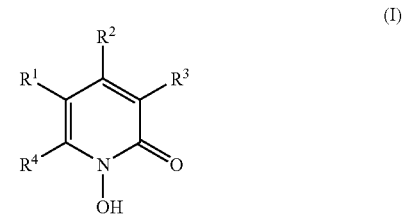

or a physiologically tolerable salt of the compound of the formula I, where $R^1$, $R^2$ and $R^3$, which are identical or different, are a hydrogen atom or alkyl having 1 to 4 carbon atoms, and $R^4$ is a saturated hydrocarbon radical having 6 to 9 carbon atoms.

A preferred pharmaceutical preparation is one where $R^4$ is a saturated hydrocarbon having 6 to 9 carbon atoms, one of the radicals $R^1$ and $R^3$ is a hydrogen atom and the other is a hydrogen atom, methyl or ethyl and $R^2$ is an alkyl radical having 1 or 2 carbon atoms.

A particularly preferred pharmaceutical preparation is one wherein the compound of the formula I contains a cyclic radical in the position $R^4$.

Furthermore preferred is a pharmaceutical preparation wherein $R^4$ is a cyclohexyl radical or —$CH_2$—$CH(CH_3)$—$CH_2$—$C(CH_3)_3$.

The term "saturated" in this case designates those radicals which contain no aliphatic multiple bonds, i.e. no ethylenic or acetylenic bonds.

Suitable compounds of the formula I which may be mentioned, for example, are 1-hydroxy-4-methyl-6-n-hexyl-, -6-iso-hexyl-, -6-n-heptyl- or -6-isoheptyl-2-pyridone, 1-hydroxy-4-methyl-6-octyl- or -6-isooctyl-2-pyridone, in particular as 1-hydroxy-4-methyl-6-(2,4,4-trimethylpentyl)-2-pyridone, 1-hydroxy-4 -methyl-6-cyclohexyl-2-pyridone, 1-hydroxy-4-methyl-6-cyclohexylmethyl- or -6-cyclohexyl-ethyl-2-pyridone, where the cyclohexyl radical can in each case also carry a methyl radical, 1-hydroxy-4-methyl-6-(2-bicyclo-heptyl)-2-pyridone, 1-hydroxy-3,4-dimethyl-6-benzyl- or -6-dimethylbenzyl-2-pyridone and 1-hydroxy-4-methyl-6-(β-phenylethyl)-2-pyridone.

The invention furthermore relates to the use of the pharmaceutical preparation for the production of a pharmaceutical for the treatment and prophylaxis of dermatomycoses.

Using the pharmaceutical according to the invention, drastic healing can be achieved in the treatment of dermatomycoses. The pharmaceutical according to the invention is also suitable for prophylactic application against dermatomycoses.

The content of the compound of the formula I in the pharmaceutical preparation according to the invention is dependent on the structure of each compound of the formula I and thus on its release from the gel, its penetration behavior in the skin and its antimicrobial properties.

In the pharmaceutical preparation according to the invention, the compound of the formula I is in general contained in an amount from 0.05 to 2 percent by weight, preferably 0.1 to 1% by weight.

Possible gel-forming agents are native substances such as gelatin, pectin, carrageenan, agar, tragacanth and alginates, semisynthetic gel-forming agents such as cellulose ethers (methylcellulose, ethylcellulose, hydroxyethylcellulose, hydroxypropylcellulose, sodium carboxymethyl-cellulose), starch derivatives and pectin derivatives and also fully synthetic gel-forming agents such as polyacrylates, polymethacrylates, polyvinyl alcohol and polyvinylpyrrolidones. Polyacrylates are particularly suitable. They are employed in amounts from 0.3 to 2.0 parts by weight to 100 parts by weight of final product.

Suitable solvents are water and also all solvents miscible with water. Those suitable are, for example, alkanols such as ethanol or isopropyl alcohol, and also propylene glycol and dimethyl sulfoxide. One or more solvents can be employed in the preparation of the formulations according to the invention.

Suitable additional solubilizers for the pharmaceutical preparation according to the invention are:

Benzyl alcohols, 2-octyldodecanol, adipates, propylene glycol and glycerol. These solubilizers are contained in the preparations according to the invention from 1 to 15 percent by weight (% by weight).

Suitable further auxiliaries are emulsifiers, wetting agents and spreading agents.

The preparations are prepared in a manner known per se by combining the individual components and—if necessary—further processing suited to the particular preparation.

The present invention is explained in greater detail by the following examples, but is not restricted to these. If not stated otherwise, the quantitative data relate to the weight.

EXAMPLE 1

A preparation according to the invention has the following composition:

| | |
|---|---|
| 1-Hydroxy-4-methyl-6-(2,4,4-trimethylpentyl)-2(1H)pyridone | 0.50% |
| Hydroxyethylcellulose | 1.50% |
| Polyethylene glycol-7 glycerylcocoate | 5.00% |
| 1,2-propylene glycol | 10.00% |
| Isopropyl alcohol | 20.00% |
| Demineralized water | 63.00% |

EXAMPLE 2

A preparation according to the invention has the following composition:

| | |
|---|---|
| 1-Hydroxy-4-methyl-6-cyclohexyl-2(1H)pyridone | 1.00% |
| Polyacrylic acid polymer (e.g. Carbomer 934 P) | 0.70% |
| Sodium hydroxide | 0.20% |
| Sodium dioctylsulfosuccinate | 0.05% |
| 2-octyldodecanol | 7.50% |
| Isopropyl alcohol | 25.00% |
| Demineralized water | 65.55% |

EXAMPLE 3

A preparation according to the invention has the following composition:

| | |
|---|---|
| 1-Hydroxy-4-methyl-6-cyclohexyl-2(1H)pyridone | 0.50% |
| Polyacrylic acid polymer (e.g. Carbomer 940) | 0.50% |
| Sodium hydroxide | 0.20% |
| Polyoxyethylene(20)sorbitan monostearate | 3.50% |
| Isopropyl myristate | 10.00% |
| Ethanol | 20.00% |
| Demineralized water | 65.30% |

EXAMPLE 4

A preparation according to the invention has the following composition:

| | |
|---|---|
| 1-Hydroxy-4-methyl-6-(2,4,4-trimethylpentyl)-2(1H)-pyridone | 1.00% |
| Hydroxypropylcellulose | 1.00% |
| 1,2-Propylene glycol | 2.50% |
| Ethanol | 20.00% |
| Demineralized water | 75.50% |

EXAMPLE 5

An ointment preparation from the prior art has the following composition:

| | |
|---|---|
| 1-Hydroxy-4-methyl-6-cyclohexyl-2(1H)pyridone | 1.00% |
| Petroleum jelly | 20.00% |
| Stearyl alcohol | 15.00% |
| 2-Octyldodecanol | 10.00% |
| Polyoxyethylene(20)sorbitan monostearate | 3.50% |
| Sorbitan monostearate | 1.50% |
| Demineralized water | 49.00% |

EXAMPLE 6

Activity Testing

Testing the active compound release of the pharmaceutical preparation according to the invention in a penetration model using excised pig's skin.

The testing of the active compound release from the compositions according to the invention was carried out in a penetration model on excised pig's skin. Here, a conclusion is drawn indirectly on the active compound release from the compositions according to the invention via the determination of the penetration depth by means of a microbiological determination method:

Relatively large pieces of back skin were excised from slaughtered pigs before scalding the killed animals, wrapped with moist paper and plastic film and deep frozen at −20° C. until the test.

Before the test, the skin surface was freed from fatty tissue, shaved and treated with isopropanol for 60 minutes for disinfection purposes. For each test batch a separate piece of skin (about 2×3 cm) was used. The skin surface was treated with preparations containing various compounds of the formula 1. After the end of the various action times (0.5, 1 and 4 hours), the products were removed from the skin surface by washing. In order to investigate the different penetration power of the active compounds—or the different release power of the preparations—the pieces of skin were stripped off 2×, 6× and 10× using Scotch film on, in each case, three adjacent tracks. Each track was then inoculated 10× in a punctiform manner with a suspension of Trichophyton mentagrophytes 100/25 (about 200 microconidia per inoculation point). The pieces of skin were then incubated at 28° C. for 7 days on water and agar with penicillin, streptomycin and cycloheximide addition. From the 4th day of incubation onwards, the result was daily read off macroscopically.

RESULTS

After a time of action of the active compound-containing gel preparations, according to Examples 1 to 4, of 4 hours, the pieces of skin are macroscopically fungus-free on all sections—in contrast to the corresponding placebo preparations.

For the active compound-containing ointment preparation not according to the invention, according to Example 5, which was prepared according to the prior art, the time of action of 4 hours is not sufficient to kill the macroconidia on the inoculated segments.

The invention claimed is:

1. A method of treatment or prophylaxis of dermatomycoses comprising administering a composition in a pharmacologically effective amount to a patient in need thereof wherein the composition is a gel composition and comprises:
    at least one hydrophilic gel-forming agent;
    at least one spreading agent; and
    an active component consisting essentially of at least one compound chosen from a compound of formula (I) and physiologically tolerable salts thereof:

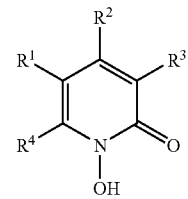

wherein $R^1$, $R^2$, and $R^3$, which are identical or different, are a hydrogen atom or alkyl group having 1 to 4 carbon atoms, and $R^4$ is a saturated hydrocarbon radical having 6 to 9 carbon atoms; and
    wherein the composition is substantially free of any additional active components.

2. The method of claim 1, wherein the active component consists essentially of 1-hydroxy-4-methyl-6-cyclohexyl-2(1H)pyridone, at least one physiologically tolerable salt thereof, or a mixture of the foregoing.

3. The method of claim 1, wherein the active component consists essentially of 1-hydroxy-4-methyl-6-(2,4,4,-trimethylpentyl)-2(1H)pyridone, at least one physiologically tolerable salt thereof, or a mixture of the foregoing.

4. A method of treatment or prophylaxis of fungus of the foot comprising administering a composition in a pharmacologically effective amount to a patient in need thereof wherein the composition is a gel composition and comprises:
    at least one hydrophilic gel-forming agent;
    at least one spreading agent; and
    an active component, wherein the active component consists essentially of 1-hydroxy-4-methyl-6-cyclohexyl-2(1H)pyridone; and
    wherein the composition is substantially free of any additional active components.

5. A method of treatment or prophylaxis of fungus of the foot comprising administering a composition in a pharmacologically effective amount to a patient in need thereof wherein the composition is a gel composition and comprises:
    at least one hydrophilic gel-forming agent;
    at least one spreading agent; and
    an active component, wherein the active component consists essentially of 1-hydroxy-4-methyl-6-(2,4,4-trimethylpentyl)-2(1H)pyridone; and
    wherein the composition is substantially free of any additional active components.

* * * * *